US000001065H

United States Statutory Invention Registration [19]

[11] Reg. Number: H1065

Salter et al.

[43] Published: Jun. 2, 1992

[54] TRANSGENIC AVIAN LINE RESISTANT TO AVIAN LEUKOSIS VIRUS

[75] Inventors: Donald W. Salter, Haslett; Lyman B. Crittenden, Williamston, both of Mich.

[73] Assignee: The United States of America as represented by the Secretary of Agriculture, Washington, D.C.

[21] Appl. No.: 217,994

[22] Filed: Jul. 12, 1988

[51] Int. Cl.[5] ..... C12N 15/00

[52] U.S. Cl. ..... 800/2; 800/DIG. 1; 435/172.3

[56] References Cited

PUBLICATIONS

D. S. Falconer, Introduction to Quantitative Genetics, Preface, Chapter 3, pp. 48–49, (1960), The Ronald Press Company, New York, N.Y.

L. B. Crittenden et al., "Gene Insertion: Current Progress and Long-Term Goals", Avian Dis., 30(1):43–46 (1985).

L. B. Crittenden et al., "Genetic Engineering to Improve Resistance to Viral Diseases of Poultry: A Model for Application to Livestock Improvement", Can. J. Anim. Sci., 65:553–562 (Sep. 1985).

Donald W. Salter et al., "Gene Insertion into the Chicken Germ Line by Retroviruses", Poult. Sci., 65:1445–1458 (1986).

D. W. Salter et al., "Chickens Transgenic for a Defective Recombinant Avian Leukosis Proviral Insert Express Subgroup A Envelope Glycoprotein", Poult. Sci. Abstracts of Papers, 66:170 (Jul. 1987).

*Primary Examiner*—Elizabeth C. Weimar
*Assistant Examiner*—Jasemine C. Chambers
*Attorney, Agent, or Firm*—M. Howard Silverstein; John D. Fado; Curtis P. Ribando

[57] ABSTRACT

A transgenic avian line, which is resistant to infection by avian leukosis virus (ALV), subgroup A, has been produced. The line was discovered as a chance event occurring in a program of infecting embryonic chickens with a recombinant ALV virus, selecting individuals assayed to be positive for genomic insertion of proviral sequences, and backcrossing to the original line to obtain G1 progeny demonstrating stable inheritance of the inserts. Of at least three proviral inserts defective for ALV production, one was found to be capable of expressing in the cell membrane subgroup A envelope glycoprotein which specifically interferes with infection by subgroup A virus. This insert represents an artificially introduced dominant gene for ALV disease resistance. Through an appropriate breeding program, a line of chickens homozygous for this gene has been obtained.

6 Claims, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

TRANSGENIC AVIAN LINE RESISTANT TO AVIAN LEUKOSIS VIRUS

BACKGROUND OF THE INVENTION

1. Field of the Invention

The raw material for animal improvement is genetic variation. Increasing genetic variability as a base for increased progress in animal breeding has been a long-term goal of agricultural research. Recent advances in molecular genetics open the possibility for transferring new genetic information to the germ line of various species. Desirable genes could then be introduced into an improved line of domestic animals and these strains used for further improvement. For example, in chickens, egg production strains are highly susceptible to avian leukosis virus (ALV). ALV is a common retrovirus of chickens that induces a B cell lymphoma called lymphoid leukosis and other neoplasms and also results in losses of productivity in mature chickens. The initial steps in the infection of chicken cells by ALV is the attachment of the retrovirus envelope glycoprotein to the cell membrane and transport of virion contents to the cytoplasm. The specificity of binding or penetration of the virion is determined by the viral envelope glycoprotein. This specificity has been used to classify ALV into different subgroups by a phenomenon called interference. Retroviruses are prevented from infecting chicken cells that were previously infected with the same subgroup by specific physical inhibition of viral absorption or penetration.

Efforts to reduce the rate of congenital infection are underway by commercial breeders. Single recessive genes for resistance to infection by each subgroup of ALV exist in chickens, but their frequency is low in egg-producing strains, and few resistant commercial strains have been developed. Introduction of a dominant gene for resistance to ALV infection in available egg production strains would achieve this goal and at the same time demonstrate that other economically important new genes can be introduced into the genome of a food animal species without disrupting the breeding program.

2. Description of the Prior Art

Natural insertion of genetic information into the chicken germ line has been occurring since the speciation of the chicken [Frisby et al., Cell 17: 623–634 (1979); Astrin et al., Cold Spring Harbor Symposium 44: 1105–1109 (1980); and Hughes et al., Cold Spring Harbor Symposium 44: 1077–1091 (1980)]. At least 22 endogenous viral genomes (proviruses) have been identified and characterized in the White Leghorn. Many more exist in other commercial lines of chickens [Hughes et al., Virology 108: 222–229 (1981); Gudkov et al., J. Gen. Virol. 57: 85–94 (1981)]. The presence of these proviruses suggests that there is a natural mechanism for proviral integration into the germ line. Presumably, retroviral infection of germ cells occurs on rare occasions.

Crittenden et al. [Avian Dis. 30(1): 43–46 (1985)] proposed a method for providing resistance to subgroup A ALV based on an endogenous ALV model of interference. Chicken embryo fibroblasts (CEF) expressing subgroup E envelope glycoprotein coded for by the defective endogenous proviral genes, ev3 and ev6, are many times more resistant to subgroup E Rous sarcoma virus (RSV) infection than CEF lacking these genes. Furthermore, chickens carrying ev3 and ev6 are resistant to subgroup E ALV infection [Robinson et al., J. Virol. 40: 745–751 (1981)]. Salter et al. [Poult. Sci. 65: 1445–1458 (1986)] have previously described the insertion of avian leukosis proviral DNA into the germ line of the chicken using recombinant and wild-type ALV belonging to subgroup A. By injecting infectious retrovirus into fertile eggs at the day of incubation and testing the resulting viremic males for genetic transmission or proviral DNA to their progeny, they conclusively showed that proviral DNA had been inserted into the chicken germ line.

SUMMARY OF THE INVENTION

We have now for the first time developed a transgenic avian line which is genetically resistant to ALV, subgroup A. This line was produced by infecting early chicken embryos with recombinant ALV and initially selecting for individuals having chromosomal proviral inserts which were defective for infectious ALV production. One such individual has been identified which is further characterized by having a genomic insert which expresses subgroup A envelope glycoprotein. Chick-embryo fibroblasts produced from individuals heterozygous for the insert were assayed to be about 5000-fold more resistant to subgroup A sarcoma virus than cultures prepared from chickens lacking the insert, but equally susceptible to subgroup B sarcoma virus. The recombinant ALV proviral insert characteristic of this novel line therefore represents an artificially introduced dominant gene for resistance to subgroup A leukosis-sarcoma viruses.

In accordance with this discovery, it is an object of the invention to introduce a novel line of transgenic chickens which is resistant to pathogenic subgroup A ALV infection.

Another object of the invention is to provide a population of chickens which can be used in a breeding program to transfer the ALV-resistant trait to other lines of chickens.

A further object of the invention is to produce a model transgenic avian line for introduction of other desirable traits by means of recombinant inserts.

It is also an object of the invention to produce a subline of chickens which are homozygous for the dominant ALV-resistant gene.

Other objects and advantages of this invention will become readily apparent from the ensuing description.

GLOSSARY

Figure 1:
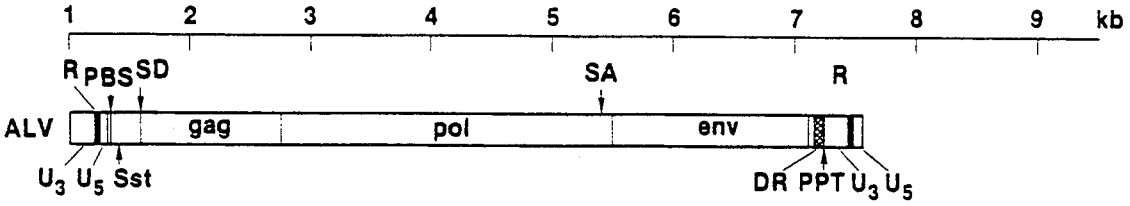
FIG. 1 is a molecular map of an avian leukosis virus (ALV).

For purposes of this invention, the following abbreviations, terms, and gene nomenclature used herein have been defined below. Also listed are the cleavage sites of the restriction enzymes referred to in the specification.

| Abbreviations | |
|---|---|
| ALV = | avian leukosis virus (exogenous oncogenic virus) |
| bp = | basepair |
| C/E = | resistant to viral subgroup E |

-continued

| Abbreviations | |
|---|---|
| C/O = | resistant to no viral subgroup |
| CEF = | chicken embryo fibroblasts |
| DR = | direct repeat |
| ev = | endogenous virus - used in conjunction with a number to identify loci in chicken genome |
| G0 = | generation of host infected with an exogenous virus |
| G1 = | first generation progeny of G0 |
| G2 = | second generation progeny of G0 |
| kb = | kilobases (1000 basepairs) |
| LTR = | long terminal repeat |
| PBS = | primer binding site |
| 3H-RSV = | Bryan high-titer Rous sarcoma virus |
| G3 = | third generation progeny of G0 |
| G4 = | fourth generation progeny of G0 |
| RPL-42 ALV = | ΓA1 |
| p27 = | ALV gag protein |
| PPT = | polypurine tract |
| RAV-0 = | Rous-associated virus, Type 0 (endogenous, nononcogenic chicken virus) |
| RAV-0-A(1) = | natural recombinant virus derived from RAV-0 |
| RAV-1 = | Rous-associated virus, biologically cloned |
| 882/-16 RAV-O = | recombinant ALV vector |
| RSV = | Rous sarcoma virus (exogenous, oncogenic chicken virus) |
| SA = | splice acceptor |
| SD = | splice donor |

Terms clone: in reference to DNA, the product or process of isolating a segment of DNA, linking it to a replicon, and introducing it into a host for expansion coding region: a region of genetic information (RNA or DNA) that encodes a particular protein or polypeptide endogenous: refers to DNA provirus which is principally passed vertically (in the genome) from one host generation to another exogenous: refers to retrovirus which infects its host by horizontal passage from one animal to another, or congenitally to progeny expression: the transcription of a gene into messenger RNA (mRNA) and the subsequent translation of the mRNA into a protein coded by the gene infection: the introduction of bacteria or virus into cells or into a living organism wherein the bacteria or virus can replicate noncoding region: a region of genetic information (RNA or DNA) that does not encode a protein or polypeptide subgroup: used in conjunction with capital letter to designate particular ALV based upon specificity of the retrovirus envelope protein toward binding of the virion to the cell membrane and penetration to the cell subclone: in reference to DNA, the product or process of cloning a portion of an already cloned DNA segment transfection: introduction of new genetic material into a cell transgenic: relating to new genetic information becoming embedded into a germ line vector: a derivative of a virus or plasmid constructed by recombinant DNA techniques and having a cloning site or sites for inserting new DNA or RNA sequences

Gene Nomenclature alv6: proviral insert expressing ALV subgroup A envelope glycoprotein env: retroviral gene which encodes the envelope antigens that determine the antigenic and subgroup specificity of the progeny virus gag: retroviral gene which encodes group-specific or internal antigens pol: retroviral gene which encodes reverse transcriptase and the endonuclease

| Restriction Enzyme | Cleavage Site |
|---|---|
| BamHI | G ↓ GATCC |
| EcoRI | G ↓ AATTC |
| SacI | GAGCT ↓ C |
| SstI | GAGCT ↓ C |

DETAILED DESCRIPTION OF THE INVENTION

FIG. 1 schematically illustrates the linear structure of an ALV virus. At the top of the drawing is a scale in kilobases. Represented in the drawing are the principal sequences of interest. The three genes required for viral replication, gag, pol, and env, are indicated. These are called the "coding sequences" or "coding regions" required for viral replication. Gag encodes the group-specific or internal antigen. Pol encodes reverse transcriptase which copies the RNA into a linear provirus DNA and also the endonuclease required for insertion of the DNA genome of the virus into the genome of the host. Env encodes the envelope antigens that determine the antigenic and subgroup specificity of the progeny virus. The complete virus particle is formed at the cell membrane and buds from it. There are several distinct envelope antigens of the exogenous ALV's that are called subgroups A through D.

The endogenous proviruses known to occur in avians are inherited as single gene loci which are sometimes transcribed and expressed. All endogenous env genes characterized so far in the chicken encode subgroup E envelope antigen that is readily distinguished from the exogenous env products. In addition to the coding sequences, retrovirus contain several important noncoding regions. The two ends of the viral genome include the regions labelled $U_3$, R, and $U_5$ which are copied by reverse transcriptase to form direct repeats found at the ends of the proviral DNA. These long terminal repeats (LTRs) are important for efficient integration into the host genome and serve as promoters for the transcription of the viral genome and messenger (m)RNA. During the viral life cycle, a viral DNA molecule is inserted into the host chromosome at a large number of sites. Host enzymes transcribe the DNA to viral genomic RNA and mRNA that is translated to form viral proteins. To the right of the left hand LTR is the primer binding site (PBS) which binds a host tRNA to permit the proper initiation of viral DNA synthesis. Also illustrated are an SstI restriction enzyme site just downstream from the PBS, a splice donor (SD), a splice acceptor (SA), a direct repeat sequence, and the polypurine tract (PPT), all of which will be described in further detail below.

The ev2 endogenous locus in the chicken genome produces the replication-competent, Rous-associated virus, (RAV-0), that has little or no oncogenic potential in vivo and has considerable homology with the ALV viruses. We and others have accumulated sufficient evidence that at least a portion of the oncogenic potential resides in the LTRs at the end of the viral genome.

The LTRs contain the promoters and polyadenylation signals necessary for appropriate expression of the viral RNAs. Furthermore, the LTRs recombine with the host genome when viral DNA integrates therein to form the provirus. The major differences between the RAV-0 LTR and the other replication-competent ALV LTRs lie in the $U_3$ segment of the LTR. The sequence of the RAV-0 LTR and adjoining regions is given in Hughes [J. Virol. 43(1): 191–200 (Jul. 1982)]. The ALV LTR contains a powerful enhancer that the RAV-0 LTR lacks. Accordingly, the RAV-0 virus replicates somewhat less efficiently than the corresponding ALVs. It seems likely that the lack of oncogenicity is also related to the absence of the powerful enhancer in the RAV-0 LTR.

The virus used in producing the subject transgenic avian line was RAV-0-A(1) of Wright and Bennett, reported by Salter et al. [Poult. Sci. 65: 1445–1458 (1986)]. RAV-0-A(1) is a natural recombinant virus obtained by infecting C/O (susceptible to all subgroups of ALV) CEF with RAV-0 and transfecting with the internal 3.8 kb Eco RI fragment of cloned Prague A viral DNA [Highfield et al., J. Virol. 36: 271–279 (1980)], which contains the polymerase gene and subgroup A envelope determinant, and selecting for subgroup A recombinants on C/E (resistant to subgroup E ALV) cells. It is mostly RAV-0-like in molecular character. The precise points of recombination are not defined; however, none, part, or all of the polymerase gene and, at least, part of the subgroup A envelope gene are derived from Prague RSV-A.

Figure 2:
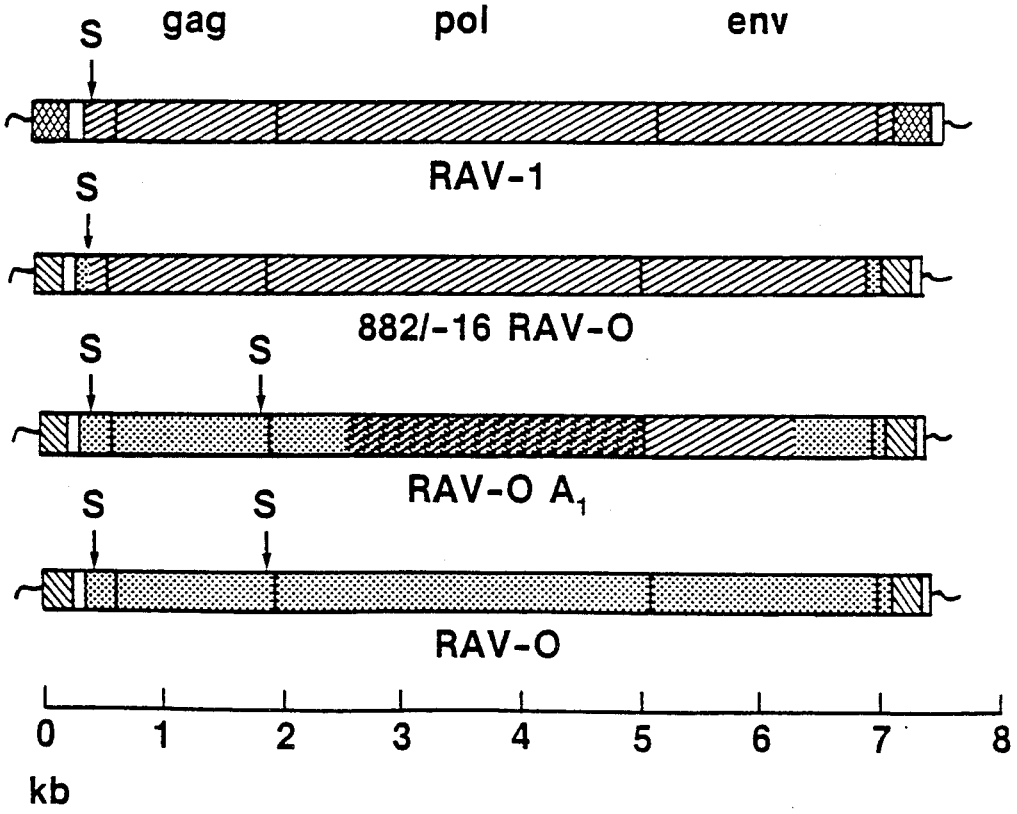
FIG. 2 is a sequence of schematic diagrams illustrating the relative construction of various ALV-type retroviruses and vectors.

FIG. 2 and Table I compare the molecular characteristics of RAV-0-A(1) to RAV-0(described above), RAV-1 (a biologically cloned avian leukosis virus), and 882/-16 RAV-0 [a recombinant ALV described by Hughes et al. in Poult. Sci. 65: 1459–1467 (1986) and the subject of commonly assigned copending application by Hughes et al., Ser. No. 07/80,278, filed Jul. 31, 1987]. To summarize, the recombinant 882/-16, RAV-0 is a molecularly engineered viral vector having only RAV-0 LTR with the entire coding regions derived from a subgroup A retroviral vector.

In FIG. 2, as in FIG. 1, the coding regions for each proviral form are: gag, group-specific antigens; pol, polymerase; and env, envelope. The LTRs are represented at the ends of the integrated proviral genomes by enclosed and open boxes. Note that the LTR from RAV-1 is approximately 100 bases longer than the LTR from RAV-0, and both recombinant viruses, RAV-0-A(1) and 882/-16 RAV-0, contain the RAV-0 LTR and variable amount of the coding regions of RAV-0 and RAV-1 as illustrated. RAV-0-like coding sequences are indicated by the dotted area and RAV-1-like sequences by the hatched area. Also note that most of the polymerase gene in RAV-0-A(1) could be either like RAV-0 or RAV-1. S with an arrow indicates SacI restriction enzyme sites in the proviral genome. Host DNA is indicated by a wavy line.

TABLE I

The Molecular Characteristics of the Retroviruses Shown in FIG. 2

| Virus | Prototype | Viral genes[a] | | | | |
|---|---|---|---|---|---|---|
| | | $LTR_l$ | gag | pol | env | $LTR_r$ |
| Endogenous | RAV-0 | N[b] | N | N | N | N |
| Exogenous | RAV-1 | X[c] | X | X | X | X |
| Recom- | RAV-O-A(1) | N | N | N or X | N or X | N |

TABLE I-continued

The Molecular Characteristics of the Retroviruses Shown in FIG. 2

| Virus | Prototype | Viral genes[a] | | | | |
|---|---|---|---|---|---|---|
| | | $LTR_l$ | gag | pol | env | $LTR_r$ |
| binant | 882/-16, RAV-0 | N | X | X | X | N |

[a]Nomenclature: $LTR_l$ and $LTR_r$ noncoding long terminal repeats left and right, respectively; gag, group specific internal antigens; pol, polymerase; env, envelope.
[b]Endogenous origin.
[c]Exogenous origin.

Table II below compares the biological characteristics of RAV-0A(1) with those of RAV-0, RAV-1, and 882/-16 RAV-0. Its oncogenicity is similar to 882/-16 RAV-0, and congential infection of progeny from viremic females is moderate compared to the other viruses.

Potential approaches for infecting avian embryos with retroviruses have been described by Crittenden et al. [Avian Dis. 30(1): 43–46 (1985)] and Crittenden et al. [Can J. Anim. Sci. 65: 553–562 (Sep. 1985)]. One such approach involves injecting the virus into multiple developing ova before ovulation [Shuman et al., Poult. Sci. 65: 1436–1444 (1986)]. This procedure exposes ova to the virus at the very early stages of development. The second approach involves binding the virus to sperm with an agent such as DEAE dextran or polybrene. Upon conventional artificial insemination of the female, the virus would presumably be carried by the sperm into the ovum. In accord with the third approach, the virus is injected in or near the germinal disc of newly laid fertile eggs. At this stage the embryo is made up of thousands of cells, but germinal primordia are still susceptible to infection. We have in fact now discovered that at least the latter approach to germ line insertion is feasible when applied to the RAV-0-A(1) virus. Successful insertion is evidenced by stable inheritance after conventional breeding. That is, the gene of interest is inherited and expressed in a Mendelian fashion.

The RAV-0-A(1) insert, coding for the subgroup A envelope glycoprotein antigen and referred to as alv6, represents a dominant gene. Upon expression and localization in the cell membranes, the antigen interferes with infection by subgroup A ALV. Chickens carrying this trait can be entered into breeding programs to confer subgroup A ALV resistance to other avian lines.

TABLE II

Approximate Mortality with Neoplasms and Vertical Transmission in Viremic Adult Chickens of Viruses Shown in FIG. 2

| Virus | Subgroup (env) | Oncogenicity[a] (%) | Transmission (%) Female | Transmission (%) Male |
|---|---|---|---|---|
| RAV-0 | E | 0–5 | 50–100[b] | 50–100[d] |
| | | | 0–10[c] | ?[e] |
| RAV-1 | A | 70–100 | 90–100[f] | 0[g] |
| RAV-0-A(1) | A | 20–25 | 20–30[f] | ?[g] |

TABLE II-continued

Approximate Mortality with Neoplasms and Vertical Transmission in Viremic Adult Chickens of Viruses Shown in FIG. 2

| Virus | Subgroup (env) | Oncogenicity[a] | Transmission Female (%) | Transmission Male (%) |
|---|---|---|---|---|
| 882/-16, RAV-0 | A | 20–25 | 70–90[f] | ?[g] |

[a]Approximate mortality with lymphoid leukosis and related neoplasms in viremic chickens maintained to at least 300 days of age in several experiments. At least 40 chickens were observed for each virus [Hughes et al., Poult. Sci. 65: 1459–1467 (1986); Motta et al., J. Natl. Cancer Inst. 55: 685–689 (1975) for the RAV-0 data; Crittenden et al., J. Virol. 33: 915–919 (1980) for the RAV-1 data].
[b]Female transmission of subgroup E ALV when integrated in the germ line [reviewed in Crittenden (1981), supra].
[d]Male transmission of subgroup E ALV when integrated in the germ line [reviewed in Crittenden (1981) supra].
[e]Male transmission of subgroup E ALV when not integrated in the germ line.
[f]Female transmission of subgroup A ALV assumed to be largely congenital [reviewed in Crittenden (1981), supra, for RAV-1].
[g]Male transmission of subgroup A ALV has been studied [Rubin et al., Proc. Natl. Acad. Sci. USA 47: 1058–1069 (1961); Spencer et al., Cold Spring Harbor Conference on Cell Proliferation 7: 553–564 (1980)].

In interbreeding heterozygous individuals, transgenic chickens homozygous for alv6 have been obtained. There appears to be little effect on the morphology, growth, and maturity of males and females. Both males and females homozygous for alv6 are sexually mature and produce semen and eggs of reasonable fertility. Gross structural analysis of alv6 proviral DNA revealed no major alterations. Both long terminal repeats and normal size proviral internal fragments from BamHI and Eco RI were present in the restricted DNA. However, one of the two SacI restriction enzyme sites is missing but this may be due to a heterogenous mixture of recombinant retrovirus used to make the transgenic chickens.

The following examples are intended only to further illustrate the invention and are not intended to limit the scope of the invention which is defined by the claims.

EXAMPLE 1

Viremic Cells and Crude Nuclei. Secondary CEF were infected with RAV-0-A(1) virus at an approximate multiplicity of infection of 0.1 and maintained in culture for 6 days. Infected cells were trypsinized, washed in phosphate buffered saline, and resuspended in phosphate buffered saline to a concentration of $2\times10^7$ cells/ml. Crude nuclei were prepared by resuspending washed viremic cells in 10 mM Tris, 10 mM NaCl, and 3 mM $MgCl_2$ (pH 8.0) at $5\times10^6$/ml and allowing them to swell at 4° C. for 10 min. The cells were then pelleted, resuspended to the same cell concentration, and lysed by douncing 20 times in a Size B pestle Dounce. Crude nuclei were collected by centrifugation, washed once in swelling buffer, and resuspended to a concentration of $2\times10^7$ nuclei/ml.

Chickens. Line 0, a line of White Leghorn chickens lacking endogenous viral sequences and selected for susceptibility to subgroups A and B was used in all experiments with ALV and recombinant ALV viruses. All eggs, chickens, and CEF were derived from the laboratory specific pathogen-free breeding flocks that are free of ALV, reticuloendotheliosis virus (REV), and certain other common poultry pathogens as determined by periodic serological tests.

Egg and Chick Injection. Line 0 fertile eggs were placed in egg cartons large end up so that the yolk reorient, and the blastoderm will lie approximately underneath the air cell. The surface of the egg was wiped with a sterile gauze soaked in 10% Roccal II solution and then wiped with an ethanol-soaked sterile gauze. A small hole was drilled into the shell of the large end of the egg by hand, shell dust was removed with an ethanol-soaked sterile gauze, and 50 μl of RAV-0-A(1) virus ($10^5$ IU), virus-infected cells, or crude nuclei ($10^6$) prepared as described above was injected into the yoke with a repeating 3-ml syringe and ½-in 26- or 30-gauge needle. The surface of the egg was wiped again with an ethanol-soaked sterile gauze and the hole sealed with "Duco" fast-drying glue. Trial injections of dye showed that some of the material was injected into the upper yolk area just underneath or beside the blastoderm. Eggs were then incubated in a standard egg incubator. After hatching, each chick was identified by wing band, vaccinated against Marek's disease with HVT/SB-1 bivalent vaccine, and a small quantity of blood (approximately 40 μl) was removed from a leg vein with a lancet and a heparanized capillary tube. Blood was diluted into 400 μl of phosphate buffered saline containing 0.02% sodium azide and 100 units heparin/ml for dot-blot analysis or into 400-μl culture medium containing 100 units heparin/ml for virus assay. Chicks positive for ALV sequences were housed in modified Horsfall-Bauer stainless steel isolators for 4 to 6 weeks with oxytetracycline hydrochloride antibiotic.

Mating and Analysis of Progeny Chicks. Each ALV and recombinant ALV-viremic male, which is designated Generation 0 (G0) was mated to two specific pathogen free Line 0 females. It was attempted to obtain 25 or more progeny chicks, designated Generation 1 (G1), from each viremic male and as many as possible from each viremic female. A small quantity of blood was collected from each progeny chick as described above for virus and antibody assay and blot hybridization as described by Salter et al., supra. The antibody assay, an enzyme-linked immunosorbant assay (ELISA) was designed to identify the presence of the ALV gag protein, p27.

Using the dot-blot hybridization technique, G1 progeny chicks were screened from each G0 ALV viremic male for transmitted ALV genetic material. These data are summarized in Table III below.

Restriction enzyme analysis with SacI revealed that the ALV provirus present in the blood DNA of the G1 dot-blot positive progeny shown in Table III had been inserted at a single site in the chicken genome. This is evidence of transmission via infected germ cells as opposed to congenital transmission. The restriction enzyme analysis also revealed that most of the inserted proviral fragments were larger than 7 kb, the approximate size of the infecting virus, suggesting that the intact viral genome was usually inserted. Of 23 different germ line inserts, two did not express infectious virus. One of the two, alv6, expressed the subgroup A envelope glycoprotein at significant levels and interfered with subgroup A virus infection. This insert was identified as an 8.1kb SacI fragment.

In all, 11 female and 9 male G1 progeny were positive for infectious ALV with titers from $10^5$ to $10^7$ infectious units per milliliter of whole blood.

TABLE III

Frequency of Transmission of Avian Leukosis Virus (ALV) Genetic Information to the Generation 1 Progeny of Generation 0 Viremic Males Mated to Specific Pathogen Free Line 0 Females

| Virus | Wingband No. of G0 parent | G1 Progeny No. | No. dot-blot positive | Frequency (%) |
|---|---|---|---|---|
| RAV-0-A(1) | U-19725 | 75 | 1 | 1.3 |
| | U-19721 | 124 | 10 | 8.1 |
| | U-19772 | 134 | 7 | 5.2 |
| | U-19770 | 28 | 3 | 10.7 |
| | 10 others[a] | 454 | 0 | 0 |
| Total | 14 | 815 | 21 | 2.6 |

[a]Number that failed to transmit to any progeny.

One G1 female carried two proviruses and another three. The chick carrying the alv6 insert was a female identified by wing band No. U-26754 and was one of 10 descendants of G0 sire U-19721.

The G1 dot-blot positive progeny were raised to maturity, mated to specific-pathogen-free Line 0 males and females and their progeny (G2) screened for active viral genetic material in blood samples by ELISA, for viral antigens, and for integrated viral genomes by the DNA dot-blot procedure, all as previously described for the G1 progeny. G2 progeny were also screened for comparison with their parents of the sites of integration of the proviruses. All 20 G1 birds that received proviral DNA from their male parent had clonal proviral-host DNA junction fragments that were transmitted to about 50% of their progeny. In the case of parent U-26754, 17 out of 40 G2 progeny were positive for the insert. U-26754 and the positive progeny were negative for the ALV gag protein, p27.

EXAMPLE 2

CEF Assay for env Expression by alv6 Insert.

Expression of env can be measured by phenotypic mixing in a chicken helper factor assay for the presence of envelope glycoprotein. Bryan high-titer Rous sarcoma virus (BH-RSV) which produces particles that lack the envelope glycoprotein will transform 16-Q quail cells. Cocultivation of CEF that express env with the transformed 16-Q quail cells yields focus-forming pseudotype virus infectious to susceptible CEF. Males heterozygous for the proviral insert were mated with C/E Line 0 females. CEF were prepared from 11-day-old embryos and cocultivated with 16-Q cells and the supernatants were assayed for focus-forming virus. Table IV shows in duplicate cultures that only those CEF containing the proviral insert, alv6, complemented the env defect in BH-RSV to produce pseudotype focus-forming virus.

TABLE IV

Presence of Chicken Helper Factor in Chicken Embryo Fibroblasts (CEF) Carrying a Defective Proviral Insert (alv6)

| Sire | alv6 CEF | No. of foci on C/E CEF[a] | |
|---|---|---|---|
| 857 | − | 0 | 1 |
| | + | 500 | 386 |
| | + | 420 | 512 |
| | − | 0 | 0 |
| | − | 0 | 1 |
| | − | 0 | 0 |
| 858 | − | 0 | 0 |
| | + | 342 | 404 |
| | + | 416 | 412 |
| | − | 0 | 0 |

TABLE IV-continued

Presence of Chicken Helper Factor in Chicken Embryo Fibroblasts (CEF) Carrying a Defective Proviral Insert (alv6)

| Sire | alv6 CEF | No. of foci on C/E CEF[a] | |
|---|---|---|---|
| | + | 384 | 532 |
| | − | 0 | 0 |
| Line 0 | control | 0 | 0 |

[a]Results of duplicate culture.

EXAMPLE 3

CEF Assay for Specific Subgroup A Interference by alv6 Insert. If subgroup A envelope is expressed then it would be expected that specific interference may occur with infection of CEF containing the alv6 locus by subgroup A RSV. Using the same CEF described in Example 2, we have demonstrated that the CEF carrying the defective proviral insert, alv6, are highly resistant to focus formation by BH-RSV (RAV-1) (subgroup A) infection but not to BH-RSV (RAV-2) (subgroup B). Half-sibling CEF lacking alv6 were highly susceptible to both viruses. A rough calculation reveals that alv6 CEF are 5000-fold more resistant than the alv6 negative CEF to infection by a subgroup A sarcoma virus. This is about the same degree of resistance ascribed to CEF containing the ev6 locus that expresses subgroup E envelope glycoprotein and blocks subgroup E RSV infection reported previously by Robinson et al., supra.

EXAMPLE 4

In Vivo Assay for Interference by alv6 Insert. One-week-old progeny chicks from matings of heterozygenous males and Line 0 females were injected in the wing web with subgroup A BH-RSV (RAV-1). Those chickens containing the alv6 provirus were highly resistant to sarcoma induction whereas most of their hatchmates lacking alv6 had palpable tumors two weeks after injection (data not shown).

EXAMPLE 5

Long-Term In Vivo Assay for Interference by alv6 Insert. Progeny chicks from a mating of four heterozygous males with Line 0 females were injected with RPL-42 ALV (subgroup A) on the day of hatch. The presence of alv6 was determined by a dot-blot procedure on blood collected at hatch. Chicks were injected intraabdominally with $10^4$ IU RPL-42 ALV (subgroup A field strain) at day 1 and then reared intermingled in two separate isolators. Serum was collected at the indicated times (in weeks) from random samplings and the presence of subgroup A ALV and antibody to subgroup A ALV determined by standard procedures [Crittenden et al., J. Virol. 61: 722–725 (1987)]. Mortality due to lymphoid leukosis was observed throughout the experiment and calculated based on the number of chicks alive at 2 weeks through 40. As reported in Table V below, alv6 chickens showed no evidence of infection to 40 weeks of age and none developed lymphoid leukosis. Infection did not occur even though the alv6 chickens were constantly exposed to virus shed by their infected, half-sib hatchmates. The nontransgenic chickens all became viremic, some produced antibody and many died of lymphoid leukosis.

EXAMPLE 6

The female chicken U-26754 heterozygous for the alv6 insert and described in Example 1 was mated to several Line 0 males. As discussed in Example 1, 17 out of 40 G2 progeny were positive for the insert. One of the positive G2 males (wing band No. W8947) was mated to each of two positive G2 females (wing band No. W8703 and W9613) and also to its mother, U-26754. Approximately one-fourth of the progeny of these matings were homozygous for the alv6 gene as determined by progeny test with Line 0. The G3 homozygotes are identified below in Table VI. These homozygotes were mated together to produce G4 progeny homozygous for the alv6 gene.

TABLE V

Interference with Subgroup A ALV Infection and Oncogenicity in Transgenic Chickens Carrying the Defective Proviral Insert (alv6)

| | Viremia[a] Age (weeks) | | | | Antibody[a] Age (weeks) | | | Lymphoid |
|---|---|---|---|---|---|---|---|---|
| Progeny | 2 | 7 | 16 | 40 | 7 | 16 | 40 | leukosis[a] |
| alv6 + | 0/36 | 0/24 | 0/27 | 0/27 | 0/24 | 0/27 | 0/27 | 0/36[b] |
| alv6 − | 39/39 | 20/23 | 23/25 | 0/1 | 1/23 | 3/25 | 1/1 | 22/39[c] |

[a]Ratio of positive/total observed.
[b]Nine out of 36 died with no evidence of neoplasms.
[c]Sixteen out of 39 died with no evidence of neoplasms but four out of the 16 had bursa-thymus atrophy characteristic of ALV pathogenicity.

TABLE VI

G3 Homozygotes for Alv6
Heterozygous Mother × W8947 (Male G2 Father)

| W8703 (G2) | W9613 (G2) | U26754 (G1) |
|---|---|---|
| WC × 417N (male) | WC × 418F (female) | WC × 419B (male) |
| WC × 417L (female) | WC × 418Q (female) | WC × 419C (male) |
| WC × 417M (female) | | WC × 419H (female) |

The line of chickens homozygous for the alv6 dominant gene has been designated as Flock ALV6-H, and is currently maintained at the Agricultural Research Service Regional Poultry Laboratory in East Lansing Mich. This line is represented by the G3 and G4 generations referred to in Example 6 and descendants thereof, and is accessible as either livestock or frozen semen, depending upon availability.

It is understood that the foregoing detailed description is given merely by way of illustration and that modification and variations may be made therein without departing from the spirit and scope of the invention.

We claim:

1. A chicken line, derived from a strain of chickens which is susceptible to avian leukosis virus infection, which chicken line has integrated in its genome a proviral sequence which expresses an envelope glycoprotein of a noninfectious subgroup A avian leukosis virus, and is thus genetically resistant to avian leukosis virus, subgroup A.

2. A chicken line as described in claim 1 wherein the genome comprises the provirus alv6.

3. A chicken line as described in claim 2 wherein the genome is homozygous for alv6.

4. A chicken, derived from a strain of chickens which is susceptible to avian leukosis virus infection, which chicken has integrated in its genome a proviral sequence which expresses an envelope glycoprotein of a noninfectious subgroup A avian leukosis virus, and is thus genetically resistant to avian leukosis virus, subgroup A.

5. A chicken as described in claim 4 wherein the genome comprises the provirus alv6.

6. A chicken as described in claim 5 wherein the genome is homozygous for alv6.

* * * * *